(12) United States Patent
Hogan

(10) Patent No.: US 6,406,460 B1
(45) Date of Patent: Jun. 18, 2002

(54) SYSTEM AND METHOD FOR AUTOMATIC NEEDLE CHANGE WARNING

(75) Inventor: Thomas Hogan, Marietta, GA (US)

(73) Assignee: Agecom, Inc., Marietta, GA (US)

( * ) Notice: Subject to any disclaimer, the term of this patent is extended or adjusted under 35 U.S.C. 154(b) by 28 days.

(21) Appl. No.: 09/621,097

(22) Filed: Jul. 21, 2000

(51) Int. Cl.[7] ............................................. A61M 5/00
(52) U.S. Cl. ...................... 604/207; 604/240; 604/121; 604/186; 604/65; 604/245; 128/DIG. 13; 222/36; 222/46
(58) Field of Search ........................... 604/240, 65, 67, 604/121, 156, 186, 164.04, 187, 207, 208, 255, 241–243, 245–247, 131, 118; 128/912, DIG. 13, DIG. 12, DIG. 1; 222/36, 38, 46

(56) References Cited

U.S. PATENT DOCUMENTS

| | | | |
|---|---|---|---|
| 4,959,056 A | * | 9/1990 | Dombrowski et al. ...... 604/186 |
| 5,078,682 A | * | 1/1992 | Miki et al. ..................... 604/65 |
| 5,611,784 A | * | 3/1997 | Barresi et al. ............... 604/211 |
| 6,110,148 A | * | 8/2000 | Brown et al. ................ 604/207 |

* cited by examiner

Primary Examiner—Brian L. Casler
Assistant Examiner—Cris Rodriguez
(74) Attorney, Agent, or Firm—Troutman Sanders LLP; Wm. Brook Lafferty

(57) ABSTRACT

A syringe has a sensor for sensing physical contact between a syringe needle and the syringe. As the sensor detects that a syringe needle has just been installed into the syringe, a counter is set to "zero", indicating the number of injections given with the installed needle. The counter automatically and cumulatively counts each injection given to the animal during a period of continuous physical contact between the syringe and the syringe needle. When the number of cumulatively counted injections equals a predetermined maximum number of injections, a syringe needle change warning mechanism delivers a needle change warning to the operator of the syringe.

8 Claims, 3 Drawing Sheets

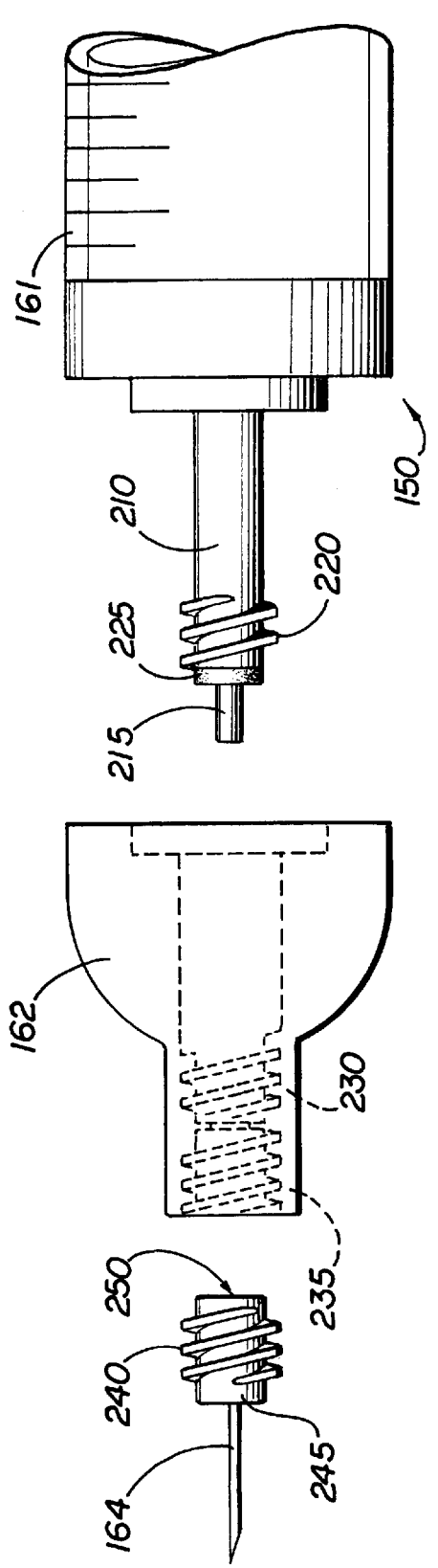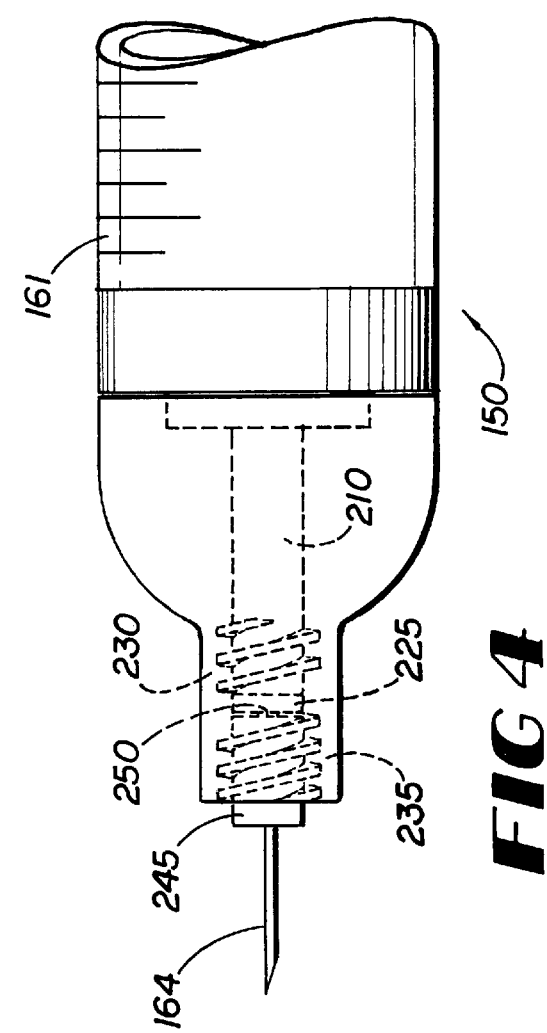

SYSTEM AND METHOD FOR AUTOMATIC NEEDLE CHANGE WARNING

TECHNICAL FIELD

The present invention relates to medicine injection systems for animals. More particularly, the present invention relates to systems and methods for alerting the user of an automated animal injection system that the syringe needle should be changed.

BACKGROUND INFORMATION

Worldwide, the agribusiness industry is facing a public acceptance crisis. In the food animal industry, increased incidences of blemished, contaminated, diseased, or over-medicated meat products have resulted diminished consumer confidence in the wholesomeness of meat protein. Furthermore, the public outcry for safe meat is forcing a flurry of more stringent federal legislation relating to source and process verification during meat production, from animal conception to public consumption.

Numerous recent advances are revolutionizing meat safety systems and processes. Specifically, the commercially available VAC-MARC® and VAC-TRAC® products, both offered by AgEcom Inc. of Marietta, Ga. 1-800-793-1671 are creating new industry standards. VAC-MARC®, one embodiment of which is taught in U.S. Pat. No. 5,961,494 (incorporated by reference herein) provides a reliable, simultaneous method of marking an animal while delivering an injection to the animal, thus eliminating accidental multiple injections or non-injection of the animal.

VAC-TRAC®, one embodiment of which is taught in pending U.S. patent application Ser. No. 09/477,262, filed Jan. 4, 2000 (also incorporated herein by reference), provides a system whereby the unique identity of an animal and information relating to injections given to the animal are automatically and electronically linked, recorded, and maintained in a central database for analysis, review and reference. Thus, the system creates for each animal a body of data relating to each and every injection given the animal, which body of data can be used for a variety of comparative, scientific and commercial purposes.

While both of these inventions represent quantum leaps in the historically technology-starved agribusiness industry, they do not address every possible avenue by which contaminants or other undesirable agents could be introduced into food animal products.

For example, in the livestock vaccination process, a single needle, attached to a syringe such as the VAC-MARC® is typically used until it is no longer serviceable because it has either (a) become too dull to easily penetrate the animal's flesh, (b) is bent, or (c) has broken off in the animal. In each case, the needle has almost certainly been used far beyond the 15–20 injections per needle recommended by Beef Quality Assurance (BQA) programs. Consequently, the likelihood of introduction of unwanted contaminants and disease have been passed to a healthy animal are significantly increased.

Accordingly, there is a need for a system and related method for determining when the number of times a syringe needle has been used.

There is another need for a system and related method for alerting a person using the syringe needle that the predetermined, recommended number of syringe needle usages have occurred.

There is yet another need for a system and related method by which use of the syringe needle is disabled upon usage of the syringe needle exceeding a maximum predetermined number of usages.

BRIEF SUMMARY OF THE INVENTION

The foregoing needs and shortcomings in prior art systems are satisfied by the present invention, which is a system for automatic needle change warning. The system comprises, generally, a syringe having a syringe needle. The syringe has a sensor for sensing physical contact between the syringe needle and the syringe. As the sensor detects that a syringe needle has just been completely and properly installed into the syringe, a counter communicatively connected to the sensor re-sets to a value of "zero", this value indicating the number of injections given with the needle which was just installed.

The counter automatically and cumulatively counts each injection given to the animal during a period of continuous physical contact between the syringe and the syringe needle. When the number of cumulatively counted injections given during the period of continuous physical contact between the syringe needle and the syringe equals a predetermined maximum number of injections, a syringe needle change warning mechanism delivers a needle change warning to the operator of the syringe. The needle change warning may be audible, visible, may disable the syringe, or may prevent any further information relating to subsequent injections from being recorded in a database.

BRIEF DESCRIPTION OF THE DRAWINGS

FIG. 3 depicts, in disassembled view, exemplary components for implementation of the present invention.

FIG. 4 depicts, in assembled view, exemplary components for implementation of the present invention.

DETAILED DESCRIPTION OF EXEMPLARY EMBODIMENTS

Figure 1:
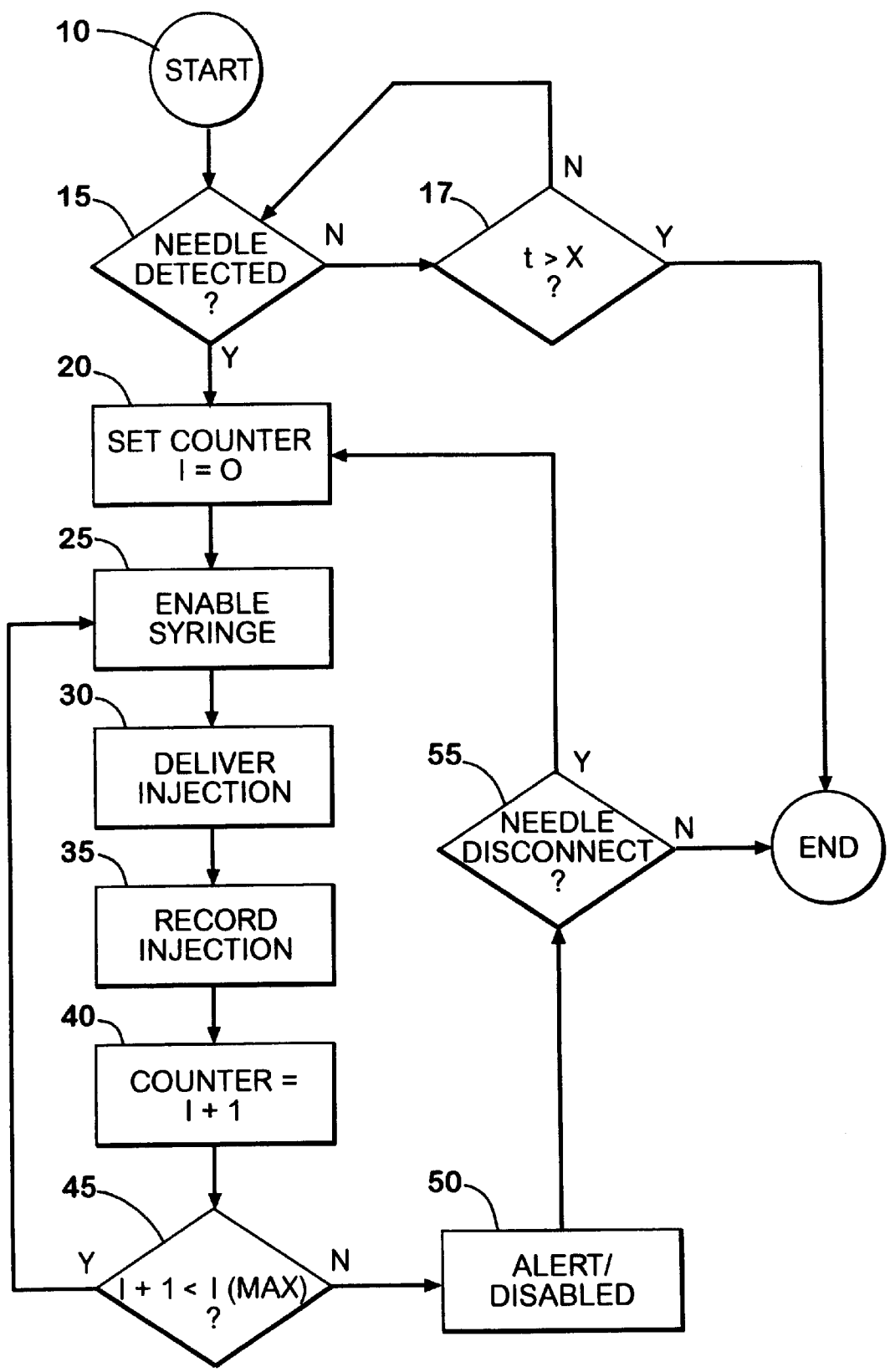
FIG. 1 depicts exemplary steps of operation of the preferred method of the present invention.

FIG. 1 depicts exemplary steps of operation of the preferred method of the present invention. More specifically, the method depicted in FIG. 1 begins at step 10 and, at decision block 15, a determination is made as to whether a syringe needle is detected attached to the syringe. As will be described in greater detail with reference to later figures, a syringe implementing the system and method of the present invention is enabled to detect the presence of a syringe needle which is properly attached to the syringe.

If the syringe needle is not properly attached to the syringe, a determination is made as to the length of time, t, that has elapsed since either the system has been turned on, or (b) a properly installed syringe needle was detected. If, as depicted in decision block 17, time t exceeds a predetermined length, the method of the present invention terminates at step 60. If time t does not exceed the predetermined length, the detecting step shown in decision block continues until either the predetermined period of time expires or a properly installed syringe needle is detected.

Once a properly installed syringe needle is detected, the injection counter is set to zero at step 20. At step 25, the syringe is enabled such as by applying power to an electrical version of the syringe, pneumatic or hydraulic pressure to air or fluid-driven versions of the syringe, or simply activating an interconnected database to accept data from the syringe.

It is significant to note that an underlying presupposition of the present invention is that its use, if proper, will ultimately provide additional guarantees of food safety to those purchasing food animal products derived from implementation of the present system and method. For a consumer to be able to recognize that such a system and method has been relied upon in production of an food animal product, an assurance must be given by the producer. Use of the present invention, in particular, use of the present invention in coordination with other systems such as the above-referenced VAC-TRAC® and VAC-MARC® systems allows a producer to make verifiable statements as to the processes used in production of the food product. Accordingly, the proper use of the present invention can be captured in a database such as those which capture information relating to the use of these other systems. In the alternative, improper use of the system and method of the present invention may be used by these other systems as a discriminator as to what data is included in the database and which data is not. In sum, it is contemplated that even if the improper utilization of the present invention (either by improper installation of a syringe needle or overuse of a syringe needle) doesn't physically disable the syringe, the data otherwise derived from its use may not be stored with data from compliant use, if stored at all. Thus, corruption of data relating to proper use of the present invention is not corrupted by data derived from improper use of the present invention.

Continuing now in the description of steps depicted in FIG. 1, after the syringe is enabled, an injection is delivered at step 30 and recorded at step 35. In its simplest form, the present invention may merely record the occurrence of the injection and the number of injections given using a particular needle. On the other hand, if the present invention is used in conjunction with either the VAC-TRAC® and/or VAC-MARC® systems, the occurrence of the injection can be linked with data such as the identity of the animal, type of medicine, etc.

Once an injection is successfully given, the counter is changed to reflect this use of the needle by incrementing the counter from I to I+1 at step 40. At decision block 45, a comparison is done to determine whether I+1 is less than I(max) where I(max) is the maximum number of injections allowed with a single needle. If I+1 is less than I(max), the method of the present invention returns to step 25, where the syringe is again enabled. If, on the other hand, I+1 is not less than I(max), the user is alerted as to the situation at step 50. Optionally, the syringe may be disabled as described earlier.

At decision block 55, an inquiry is made as to whether the syringe needle has been disconnected from the syringe. If so, the method returns to step 20, where the counter is reset to zero and the above-described process is repeated. If not, the method concludes at step 60.

Figure 2:
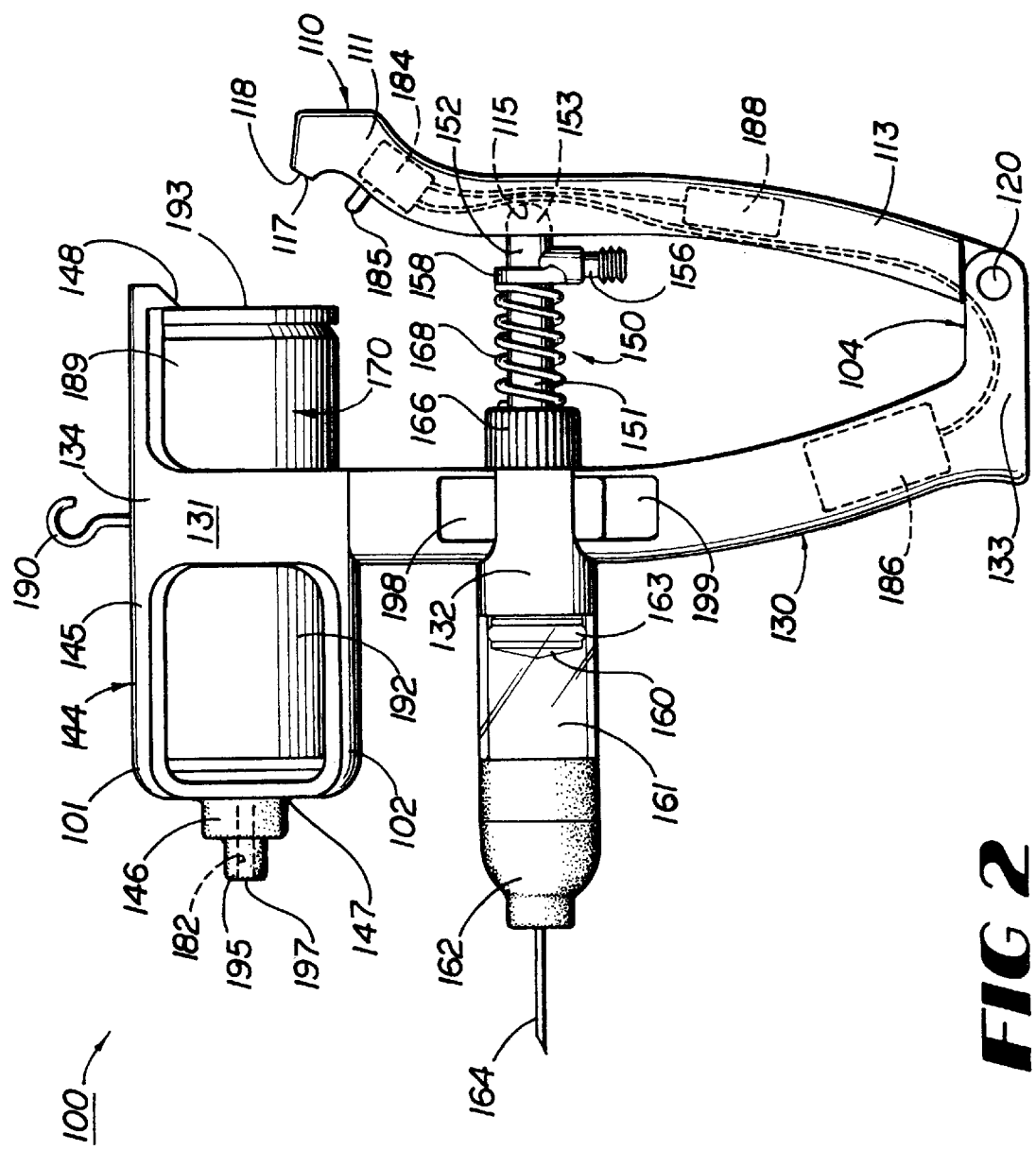
FIG. 2 depicts an exemplary embodiment of the present invention in a preferred operating environment.

FIG. 2 depicts an exemplary embodiment of the present invention in a preferred operating environment. More particularly, the system of the present invention is depicted as functionally integrated with an intelligent syringe 100. The intelligent syringe 100 comprises, generally, a syringe handle 104 operatively connected to a medicine syringe 150 and an optional ink dispenser 170. The syringe handle 104 comprises a first syringe handle 110 pivotally connected to a second syringe handle 130. The first syringe handle 110 is elongated, having a first end 111 and a second end 113. An ink dispenser interface 117 is located generally adjacent to the socket 115 on the handle 110. The handle 110 has a pivot hole in its second end 113.

The second syringe handle 130 of the intelligent syringe 100 is also elongated and has a first end 131 and a second end 133. The first end 131 of the second syringe handle 130 may securely received a hook 190 for storage of the marking syringe 100 between uses. The second syringe handle 130 is configured to function as a finger grip for the user. The second end 133 of the second syringe handle 130 is sized to slidably straddle the second end 113 of the first handle 110 and has a pivot hole through its thickness. The second handle 130 includes an integral medicine syringe collar 132 and an integral ink dispenser collar 134.

During assembly, the second end 133 of the second syringe handle 130 is positioned over the second end 113 of the first syringe handle 110 such that the pivot holes in the ends 113, 133 are axially aligned. Thereafter, a pivot pin 120 is inserted through the aligned holes and appropriately secured therein in any number of ways, including deforming distal ends of the pivot pin 120 so that the diameter of the pivot pin 120 is larger at the points of deformation than the diameter of the pivot pin receiving holes, thereby preventing withdrawal of the pivot pin 120 through the pivot receiving holes. After the pivot pin 120 is properly positioned and secured, the second syringe handle 130 rotates about the axis of the pivot pin 120 in a plane defined by the second syringe handle 130 and the first syringe handle 110. In use, the first and second handles 110, 130 are initially in a spread position. The user can then grip the first and second handles 110, 130 and squeeze them into a closed position as the handles 110, 130 pivot about the pin 120.

The medicine syringe 150 is mounted between the handles 110, 130 by means of the medicine syringe collar 132 on the second syringe handle 130 and the socket 115 on the first syringe handle 110. The medicine syringe 150 comprises a medicine syringe head 152 with a ball 153, an extendible medicine syringe shaft 151, a medicine syringe biasing spring 168, a medicine syringe plunger 160, a medicine syringe dosage chamber 161, a medicine syringe needle fastener 162, and a needle 164 (also referred to herein as a "syringe needle"). In order to connect the medicine syringe 150 to the handle 104, the dosage chamber 161 is threaded into the handle collar 132 of the handle 130, and the medicine syringe head 152 is connected to the handle 110 by engaging the ball 153 of the head 152 into the socket 115 of the handle 110 in a well known manner.

The head 152 is hollow and further comprises a medicine syringe nipple 156 and a transmitting syringe stop flange 158. The medicine syringe nipple 156 may be integral to the hollow medicine syringe head 152 and is sized to securely receive a syringe vaccine hose (not shown). Vaccine is delivered to the hollow interior cavity of the head 152 via the vaccine hose which is connected to a vaccine source (not shown). The medicine syringe stop flange 158 extends laterally about the periphery of the medicine syringe head 152.

The extendible medicine syringe shaft 151 interconnects the syringe head 152 and the plunger 160. The shaft 151 has an interior axial conduit (not shown) which communicates at one end with the interior cavity of the head 152 and at the other end with an interior axial conduit (not shown) through the plunger 160. The syringe shaft 151 extends through a medicine syringe collar 132 of the second syringe handle 130 and into the vaccine dosage chamber 161. In order to vary the amount of the dosage, the shaft 151 has a vaccine dosage adjust valve 166. The dosage adjust valve 166 comprises a collar that engages the plunger 160 on one end and is threaded onto the syringe shaft 151.

In the depicted syringe embodiment, a dosage signal is transmitted to the intelligent syringe 100 and the intelligent syringe 100 automatically varies the dosage amount depending on the size of the animal 40 (and possibly other factors, as well), a controller 198 is functionally connected to the dosage adjust valve 166. More particularly, the controller 198 comprises a receiver 199 for receiving the dosage signal 61 from the transmitter 186. The controller 198 possesses the requisite intelligence (by way of internal microprocessor) to convert the dosage signal 61 into an action command for the dosage adjust valve 166. Thereafter, the controller 198 automatically adjusts the dosage adjust valve 166 to provide the proper dosage to the animal 40 via simple mechanical linkage such as that which is well known in the art.

The dosage receiver 199 and the controller 198 are powered by a power source such as power source 188, illustrated as positioned within the intelligent syringe 100. Alternately, the controller 198 and dosage receiver 199 may be powered by an external power source (not shown).

After automatic adjustment of the dosage adjust valve 166, and actuation of the intelligent syringe 100, the medicine syringe plunger 160 slides within the vaccine dosage chamber 161. An O-ring 163 creates a liquid tight seal between the periphery of the plunger 160 and the interior wall of the dosage chamber 161. The plunger 160 has a check valve (not shown) within its interior axial conduit that allows liquid to pass only in the direction toward the needle end of the syringe 150.

The medicine dosage chamber 161 is formed of a translucent or transparent material and is secured at its first end to the medicine syringe collar 132. The medicine dosage chamber 161 may be scored with incremental graduations to assist a user in dosage measurements. At its second end, the medicine dosage chamber 161 removably receives a syringe needle fastener 162. The syringe needle fastener 162 is fitted to capture a needle 164, as will be described in greater detail with reference to later figures. A check valve (not shown) is fitted within the syringe needle fastener 162 to allow liquid flow only out of the needle 164.

A syringe biasing spring 168 is disposed around the medicine syringe shaft 151 between the medicine syringe stop flange 158 and the vaccine dosage adjust valve 166. The biasing spring 168 is a compression spring which serves to return the syringe handles 110, 130 to their initial spread position after being squeezed closed by the user.

When the handles 110, 130 are squeezed together, the plunger 160 moves within the dosage chamber 161. The movement of the plunger 160 closes the check valve within the plunger 160 to force vaccine in the dosage chamber 161 through the check valve within the needle fastener 162 and out through the needle 164. When the handles 110, 130 are released by the user, the check valve within the needle fastener 162 closes to preclude fluid or air being drawn into the dosage chamber 161 through the needle 164. Simultaneously, the check valve within the plunger 160 opens to that vaccine is drawn into the dosage chamber 161 through the nipple 156, the hollow head 152, the conduit within the shaft 151, and the conduit within the plunger 160. By turning the dosage adjust valve 166, the length of the shaft 151 is changed. Changing the length of the shaft 151 changes the length of the plunger stroke, and the amount of medicine delivered through the needle 164 is correspondingly changed.

In a preferred embodiment, the optional ink dispenser 170 comprises a self contained storage unit 189. It will be understood and appreciated that alternate embodiments may not implement this self contained storage unit 189. Nonetheless, the self contained storage unit 189 may take any number of forms well known to those skilled in the art of marking substance apparatus, including, but not limited to, a canister, a jar, a tube, or the like.

Further, the specific form of self contained storage unit 189 is dependent upon the type of ink being utilized. For instance, a pressurized canister maybe used to store ink which is suspended in, or in the form of, a compressed gas. Alternatively, a structure such as that used to store household caulk may be used to store liquid ink.

To support and retain the self contained storage unit 189, the second handle 130 may further comprise an integral retention cage 144 extending from the ink dispenser collar 134. The retention cage 144 may take any number of forms well known to those skilled in the art of mechanical design. It will be appreciated that the form of the retention cage 144 is dependent upon the physical characteristics of the self contained storage unit 189 being used.

The self contained storage unit 189 may comprise a pressurized canister 191, the ink dispenser interface 117 having a contact point 118, a retention cage 144 having a body 145, a valve actuator 146, a tip opening 147, and a can detent 148. The pressurized canister 191 may contain ink in the form of an aerosol, a non-aerosol compressed gas, or the like. The pressurized canister may be mounted to the second handle 130 my means of the collar 134 and the retention cage 144. The pressurized canister 191 comprises a canister body 192 having a bottom surface 193, a valve trigger (not shown), and an ink discharge orifice 182. In order to install the pressurized canister 191 into the handle 104, the canister body is inserted into the handle collar 134 of the second syringe handle 130 and maneuvered into the retention cage 144 until the can detent 148 makes contact with the bottom surface 193 of the canister 191, thereby securely capturing the pressurized canister 191 within the retention cage 144.

After secure capture of the pressurized canister 191 within the retention cage 144, the ink discharge orifice 182 extends through the tip opening 147, and the valve trigger is positioned in contact with, or adjacent to, the valve actuator 146. When fully inserted, the retention cage 144 assures that the bottom of the pressurized canister 191 is aligned with the radial path of rotation of the ink dispenser contact point 118 on the second syringe handle 130, as defined by rotation of the second handle 130 about the pin 120.

Importantly, it is specifically contemplated that the intelligent syringe could be pneumatic in design. More specifically, the syringe may be powered by a source of compressed air, liquid or electricity so that when the user activates a trigger, the functions previously described as effected by squeezing the handles together are accomplished.

Central to the preferred functionality of the intelligent syringe 100 is the transmitter circuitry integral to the intelligent syringe 100. The transmitter circuitry may comprise a transmit trigger 184, a transmitter 186, and a power source 188. As depicted, the transmit trigger 184 may be positioned within the handle 110 proximal to the ink dispenser contact point 117. The transmit trigger 184 supports a transmit sensor 185 positioned such that actuation of the intelligent syringe 100 by squeezing handles 110, 130 places the transmit sensor 185 in contact with the pressurized canister 191. The transmit trigger, powered by a power source 188 such as a battery, detects contact between the transmit sensor 185 and the pressurized canister 191 and relays an appropriate signal to the transmitter 186. The specific characteristics of the transmitter 186 will vary depending on the particular embodiment of the present invention being practiced, but in all cases, the transmitter is of sufficient signal strength and signal complexity to transmit, at a minimum, the injection event to a receiver.

Optionally, the intelligent syringe 100 may include a flow meter in communication with the medicine syringe 150 for detecting the amount of medicine delivered in any given actuation. In such an optional embodiment, the transmitter 150 must be of a type to be able to transmit such data to a designated receiver. Similarly, it is within the spirit and scope of the present invention that the medicine syringe 150 is capable of transmitting and facilitating the recording of the time and date on which medical treatments were given, as well as specifics of the particular treatment, such as the manufacturer of the medicine, the batch number and the date of manufacture.

FIG. 3 depicts, in disassembled view, exemplary components for implementation of the present invention. In particular, FIG. 3 depicts a preferred configuration for implementation of the needle change warning aspect of the present invention.

The medicine syringe 150 and dosage chamber 161 are characterized, at one distal end, by a medicine discharge nozzle 210 connected at its first end to the medicine syringe 150 and further having, at its opposing end, a discharge nozzle tip 215. Intermediate between opposing ends of the medicine discharge nozzle 210 are discharge nozzle screw threads 220. Importantly, the medicine discharge nozzle 210 carries a syringe contact 225. The syringe contact 225 can take a variety of forms, though its ultimate function is to detect, through either electrical connection or pressure detection, the presence of a needle such as syringe needle 164 in contact therewith. In the depicted embodiment, the syringe contact 225 is an annular metallic member having an electrical connection (not shown) to the transmitter 186.

In the depicted embodiment, the transmission of the injection event by the transmitter 186 to a receiver may contain information relating to the status of the connection between the syringe contact 225 and the needle 164, as determined by monitoring the integrity of the connection between the syringe contact 225 and the needle 164.

Continuing with the description of the embodiment depicted in FIG. 3, the needle fastener 162 is generally hollow so as to accommodate and interconnect the medicine syringe 150 to the needle 164. The preferred configuration for accomplishing this interconnection calls for screw receiving threads on the inner annular surface of the "hollow" needle fastener. In particular, medicine syringe needle threads 230 are sized and positioned to securely interrelate with the discharge nozzle screw threads 220 on the medicine discharge nozzle 210, thereby securely fastening the needle fastener 162 to the medicine syringe 150.

The needle fastener 162 also defines, by inner molding, needle receiving threads 235, which are sized and positioned to securely interrelate with needle screw threads 240 disposed about the needle head 245 of the needle 164.

FIG. 4 depicts, in assembled view, exemplary components for implementation of the present invention. The needle fastener 162 has been secured to the medicine syringe 150 by rotating the needle fastener 162 in a well known manner such that the discharge nozzle screw threads 220 become securely engaged with corresponding medicine syringe receiving threads 230. Thereafter, the syringe needle 164 is attached to the needle fastener 162 by rotating the needle about its longitudinal axis in a well known manner such that the needle screw threads 240 positioned about the needle head 245 become securely engaged with the needle receiving threads 235 within the needle fastener 162.

A central aspect of the present invention relates to the positioning of the needle head end 250 and the syringe contact 225. As previously described, and as currently illustrated, when the needle fastener is completely and properly mounted on the medicine syringe 150 and the needle 164 is completely and properly installed in the needle fastener 162, the needle head end 250 is in substantial contact with at least a portion of the syringe contact 225. Accordingly, the presence of (or absence of) a properly installed needle 164 as part of a syringe such as the intelligent syringe 100 can be detected by electrical means well known to one skilled in the art of electrical detection means.

An alternate (and somewhat less desirable) embodiment dispenses with the an electrical connection between the syringe contact 225 and the needle head end 250 being the system for detecting the proper and continuous presence of the needle 164. More specifically, it is envisioned that a pressure-sensitive contact may serve as the syringe contact 225. Such a pressure-sensitive contact would detect the urging force applied by a properly and completely installed syringe needle 164 and report, via electrical signal, to the transmitter 186 for transmission with other data to a database (not shown).

I claim:

1. A system for automatic needle change warning, comprising:

a. a syringe having a syringe needle, the syringe being functional to deliver an injection to an animal, the syringe further having a sensor for sensing physical contact between the syringe needle and the syringe;

b. a counter for automatically cumulatively counting each injection given to the animal during a period of continuous physical contact between the syringe needle and the syringe; and c. responsive to the number of cumulatively counted injections given during the period of continuous physical contact between the syringe needle and the syringe equaling a predetermined maximum number of injections, a syringe needle change warning mechanism functional to deliver to an operator of the syringe a needle change warning.

2. The system of claim 1, whereby the syringe needle change warning mechanism is functional to disable the syringe.

3. The system of claim 1, whereby the counter is operative to record the cumulative number associated with each injection.

4. The system of claim 1, whereby the counter is operative to, in response to the sensor detecting a termination of continuous physical contact between the syringe needle and the syringe, automatically re-set the cumulative count of each injection given to zero.

5. A system for automatic needle change warning, comprising:

a. a syringe having a syringe needle, the syringe being functional to deliver an injection to an animal, the syringe further having an electrical sensor proximal to a position of complete and proper installation of the syringe needle into the syringe for sensing physical contact between a head end of the syringe needle and the sensor, b. a counter for, upon initially sensing the complete and proper installation of the syringe needle into the syringe, re-setting itself to a value of zero, then automatically cumulatively counting each injection given to the animal during a period of continuous physical contact between the syringe needle and the syringe; and c. responsive to the number of cumulatively counted injections given during the period of continuous physical contact between the syringe needle and the sensor equaling a predetermined maximum number of injections, a syringe needle change warning mechanism delivering to an operator of the syringe a needle change warning.

6. The system of claim 5, whereby the syringe needle change warning mechanism is functional to disable the syringe.

7. The system of claim 5, whereby the counter is operative to record the cumulative number associated with each injection.

8. The system of claim 5, whereby the counter is operative to, in response to the sensor detecting a termination of continuous physical contact between the syringe needle and the sensor, automatically re-set the cumulative count of each injection given to zero.

* * * * *